(12) United States Patent
Brown

(10) Patent No.: US 6,248,885 B1
(45) Date of Patent: *Jun. 19, 2001

(54) BORANE-TRIALKYLAMINE HYDROBORATION AGENTS

(75) Inventor: Herbert C. Brown, West Lafayette, IN (US)

(73) Assignee: Sigma-Aldrich Co.

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/056,412

(22) Filed: Apr. 7, 1998

Related U.S. Application Data

(63) Continuation of application No. 08/437,584, filed on May 9, 1995, now abandoned.

(51) Int. Cl.$^7$ ................................................. C07C 211/00
(52) U.S. Cl. ............................................... 544/69; 564/463
(58) Field of Search ........................ 544/69, 67; 564/463, 564/403

(56) References Cited

U.S. PATENT DOCUMENTS 2,860,167 * 11/1958 Brown .................................. 260/583

* cited by examiner

*Primary Examiner*—Samuel Barts

(57) ABSTRACT

Borane-trialkylamines of the formula $$H_3B \cdot NRR^1R^2$$

wherein R is a tertiary alkyl group having 4 to 8 carbon atoms, and $R^1$ and $R^2$ are the same or different straight or branched chain alkyl from 1 to 4 carbon atoms are provided. The compounds are new hydroboration agents.

2 Claims, No Drawings

BORANE-TRIALKYLAMINE HYDROBORATION AGENTS

BACKGROUND OF THE INVENTION

This application is a continuation of 08/437,584 filed May 9, 1995 now abandoned.

FIELD OF THE INVENTION

The present invention provides a novel class of borane adducts with selected trialkylamines, and more particularly relates to borane-trialkylamines wherein at least one alkyl is a branched chain $C_4$–$C_8$ alkyl, preferably tert-butyl or tert-octyl, and their use in the hydroboration and reduction of organic compounds. The novel borane-amine adducts of this invention have a number of advantages over the presently available agents.

PRIOR ART

Borane adducts with amines are versatile reagents exhibiting many different properties as compared to the metal borohydrides. For example, they are soluble in a variety of solvents, including hydrocarbons or even water, and in some cases can be used in an acidic medium. Many adducts have been synthesized. See for example, Long, L. H. in W. J. Mellor *A Comprehensive Treatise on Inorganic and Theoretical Chemistry;* Longman: London, 1981, Supplement Vol. 5, Part B1, p 1.; and Meller, A. In Gmelin *Handbook of Inorganic and Organometallic Chemistry;* Springer: Berlin, 1992, 4th Supplement, Vol. 3, p 1. Several are commercially available. They find various uses, e.g., as fuel additives, polymerization catalysts, polymer stabilizers and stain removers, in metal plating and in the dye and pharmaceutical industries. See Lane, C. F. *Aldrichimica Acta* 1973, 6, 51. Most of these applications are based on their reducing properties.

In contrast, the use of borane-amine adducts for hydroboration is rather limited due to strong complexation, which renders their reactivity low as compared to the weaker borane adducts with ethers and sulfides. For example, borane-triethylamine does not hydroborate 1-octene at room temperature and only very slowly in refluxing tetrahydrofuran (THF). See Brown, H. C. et al. *Inorganic Chem.* 1984, 23, 2746.

Amines as borane carriers offer significant advantages often giving adducts of low sensitivity to moisture and air and readily soluble in representative solvents. Environmentally important is an easy recovery of the amine from the hydroboration products, making possible its ready recycling. The significance of these factors becomes apparent with the growing importance of diborane for the synthesis of pharmaceuticals and other valuable compounds. However, the well established reagents, borane-tetrahydrofuran and borane-dimethylsulfide (BMS) suffer a number of disadvantages for large-scale commercial applications as discussed below.

Borane-tetrahydrofuran is a valuable reagent for the hydroboration of olefins and for the reduction of organic compounds. It suffers from the disadvantage in that the solutions are unstable over a period of time. U.S. Pat. No. 3, 882, 037 discloses stabilized borane-tetrahydrofuran solutions which permit storage of such solutions for relatively longer periods of time. However, the inherent availability only as a relatively dilute solution in tetrahydrofuran poses a drawback to commercial use of this reagent.

Borane-methyl sulfide (BMS) is much more stable than borane-tetrahydrofuran and is widely used for both hydroboration and reduction [See Burg et al., *J. Am. Chem. Soc.* 76, 3307 (1954) and Coyle et al., *J. Am. Chem. Soc.* 81, 2989 (1959)]. However, it suffers from the serious disadvantage in that it yields a product which contains free dimethyl sulfide. The free dimethyl sulfide is highly volatile, b.p. 38° C., flammable and has a very noxious odor. Moreover, it is not soluble in water, so it cannot be disposed of by washing it away with water.

Borane-1, 4-thioxane (U.S. Pat. No. 4, 298, 750) is another valuable hydroboration agent. It has both lower volatility and milder odor than dimethyl sulfide. It has a limited solubility in water and can be easily oxidized to the corresponding sulfoxide, which is miscible in water. This agent is a liquid, 8 M in $BH_3$, stable over prolonged periods. Unfortunately, this commercially available reagent is relatively costly compared to borane-tetrahydrofuran and borane-dimethyl sulfide.

The growing importance of borane reagents for the synthesis of pharmaceuticals and other compounds and the problems associated with other well established borane adduct hydroboration agents, e.g., low concentration and stability, high volatility, flammability, unpleasant odor, as discussed above, create a need for easy to handle, stable and environmentally benign hydroborating agents as discussed specifically below.

Thus, the search continues for effective, versatile borane derivatives which are as effective as the commercially available reagents but which overcome the disadvantages of noxious odor, expense, volatility, and lack of water solubility. The amines of the present invention are well suited for that purpose. They have an agreeable odor, form neat adducts, are highly concentrated in borane, are soluble in various solvents, and the amine can be readily removed and recovered from hydroboration products.

It is wholly surprising that the borane-trialkylamines of the present invention are valuable hydroborating agents since the ethyl derivative is a hindered amine widely used as a proton scavenger [Raber, D. J. et al., *Tetrahedron Lett.,* 4741 (1971)] but which forms a borane adduct that hydroborates 1-octene in tetrahydrofuran in two hours at room temperature. The compounds of this invention, on the other hand, hydroborate 1-octene in tetrahydrofuran in less than an hour, and in most cases in 15–30 minutes.

SUMMARY OF THE INVENTION

The present invention provides novel borane adducts of trialkylamines represented by the formula:

$$H_3B \cdot NRR^1R^2$$

wherein R is a branched chain alkyl having 4 to 8 carbon atoms, $R^1$ and $R^2$ are the same or different straight or branched chain alkyl or alkoxy having from 1 to 5 carbon atoms, and B is boron.

Presently preferred compounds are those wherein R is tert-butyl or tert-octyl.

For ease of discussion, illustrative compounds prepared and tested are referred to with a number and letter designation as shown in the following table.

| Compound | R | $R_1$ | $R_2$ |
|---|---|---|---|
| 1a | t-Bu | —$CH_2CH_2OCH_2CH_2$ | —$CH_2CH_2OCH_2CH_2$ |
| 1b | t-Bu | Et | Et |

-continued

| Compound | R | $R_1$ | $R_2$ |
|---|---|---|---|
| 1c | t-Bu | $Pr^n$ | $Pr^n$ |
| 1d | t-Bu | —$CH_2CH_2OMe$ | —$CH_2CH_2OMe$ |
| 1e | t-Bu | $Bu^i$ | $Bu^i$ |
| 2a | t-Bu | Me | $Bu^i$ |
| 2b | t-Bu | Me | $Pr^i$ |
| 2c | t-Bu | Et | $Bu^i$ |
| 2d | t-Bu | $Pr^n$ | $Bu^i$ |
| 2e | t-Bu | Et | $Pr^i$ |
| 3a | t-Oct | Me | Me |
| 3b | t-Oct | Et | Me |
| 3c | t-Oct | —$CH_2CH_2OCH_2CH_2$ | —$CH_2CH_2OCH_2CH_2$ |
| 3d | t-Oct | Et | Et |
| 3e | t-Oct | $Bu^i$ | Me |
| 3f | t-Oct | $Pr^n$ | $Pr^n$ |

Generally speaking, the novel compounds of this invention are conveniently prepared in a straight-forward procedure by passing diborane into a neat amine at 0° C. in a bubbler provided with a stirrer. Excess diborane not absorbed by the amine is absorbed in a down-stream bubbler containing tetrahydrofuran over mercury and cooled in ice water. A mercury bubbler is connected to the exit. Diborane is passed into the amine until the concentration of excess borane in THF reaches approximately 1 M. The borane-amine adduct is stirred overnight at room temperature prior to disconnecting the bubblers and analyzed for active hydride following the procedure described by Brown, H. C., *Organic Syntheses via Boranes,* J. Wiley: New York, 1975, p. 191, using a 2 M hydrochloric acid-glycerol-water (2:1:1) hydrolysis solution.

In accordance with the invention, borane-amine adducts are prepared by passing diborane into a neat amine at temperatures in the range of 0° C. to 25° C. until no more diborane is absorbed. A solution of an amine in a suitable solvent, preferably diethyl ether, can also be used.

The complexing ability of the amines toward borane was tested by the exchange of BMS (borane-methylsulfide) and $BH_3.THF$ (borane- tetrahydrofuran) mixed in 1:1 molar ratio. The amount of borane taken by an amine in the equilibrium was determined by $^{11}B$ NMR and is shown in Tables 1, 2 and 3. Values for the exchange with borane-tetrahydrofuran, a 1 M solution, should be considered less quantitative since THF is in large excess.

The borane adducts of this invention are highly reactive, hydroborating 1-octene is tetrahydrofuran at room temperature in less than 1 hour. A number of the adducts are liquids above 0° C. The preparation of representative borane-amine adducts of this invention are illustrated in the following examples.

DETAILED DESCRIPTION OF PREFERRED EMBODIMENTS

All manipulations and reactions with air-sensitive compounds were carried out under a nitrogen atmosphere. All glassware was oven-dried for several hours, assembled while hot and cooled in a stream of dry nitrogen gas. Syringes were assembled and fitted with needles while hot. Techniques for handling air-sensitive compounds under nitrogen atmosphere are described in Brown, H. C., *Organic Syntheses Via Boranes,* J. Wiley; New York, 1975, p. 191. $^1H$, $^{13}C$ and $^{11}B$ NMR spectra were recorded on a Varian Gemini 300 multinuclear instrument. The $^{11}B$ NMR chemical shifts are δ relative to $BF_3.OEt_2$. Mass spectra were taken on a 4000 Finnigan MAT spectrometer. Optical rotations were measured on a Rudolph automatic polarimeter Autopol III. GC analyses were carried out on a Varian 3300 chromatograph (catharometer) equipped with a 12 ft×0.125 in column packed with 10% SE-30 polyethylene glycol (Union Carbide) on Chromosorb W 100–120 mesh). Microanalysis were performed at the Microanalytical Laboratory, Purdue University, West Lafayette, Ind., USA.

N-tert-butylmorpholine, N-tert-octylmorpholine and diisopropyl sulfate were prepared by literature procedures. N-tert-Butyldiethanolamine (Fluka) and other starting amines (Aldrich) were commercial products. Tetrahydrofuran was freshly distilled from benzophenone ketyl prior to use.

EXAMPLE 1 tert-Butylisobutylamine

A mixture of tert-butylamine (10.97 g, 0.15 mol), isobutyl bromide (13.70 g, 0.1 mol), adiponitrile (10.81 g, 0.1 mol) and tetrabutylammonium iodide (1.85 g, 5 mmol) was refluxed with stirring for 12 hours. Aqueous 5 M potassium hydroxide (30 ml, 0.15 mmol) was added and the mixture was extracted with n-pentane (2×50 ml). Three layers were formed. Adiponitrile (the middle layer) was recovered. The pentane solution was dried over anhydrous magnesium sulfate and the product was isolated by distillation to yield 9.5 g, (74%), bp 45–47° C./40 mm Hg; $^1H$ NMR ($CDCl_3$) δ0.91 (d, J=6.5 Hz, 6H, $CH_3$), 1.08 (s, 9H, $CH_3$), 1.64 (sep, J=6.5 Hz, 1H, CH), 2.34 (d, J=6.5 Hz, 2H, $CH_2$).

EXAMPLE 2 tert-Butylisopropylamine

A mixture of tert-butylamine (14.63 g, 0.2 mol) and diisopropyl sulfate (18.22 g, 0.1 mol) was refluxed for 1 h with stirring. The temperature rose from 58° to 83° C. Two phases formed. Aqueous 5 M potassium hydroxide (50 ml, 0.25 mol) was added. The organic layer was separated and the aqueous layer was extracted with diethyl ether (50 ml). The organic solutions were combined, dried over anhydrous magnesium sulfate and the product was isolated by distillation to yield 9.55 g (83%), bp 98–100° C./760 mm Hg. $^1H$ NMR ($CDCl_3$) δ0.95 (d, J=6.5 Hz, 6H, $CH_3$) 1.00 (s, 9H, $CH_3$), 2.93 (sep, J=6.5 Hz, 1H, CH).

EXAMPLE 3 tert-Butyldi-n-proylamine (1c)

A mixture of tert-butylamine (29.26 g, 0.4 mol), 1-iodopropane (51.00 g, 0.3 mol) and glycerol (13.81 g, 0.15 mol) was refluxed for 4 h. Aqueous 8 M potassium hydroxide (62.5 ml, 0.5 mol) was added, and the organic phase was separated and dried over anhydrous magnesium sulfate. tert-Butylamine was removed and crude tert-butyl-n-propylamine, 25.05 g, 72% yield, was obtained. It was treated with 1-iodopropane (25.50 g, 0.15 mol) and glycerol (6.91 g, 75 mmol) and the mixture was refluxed for 6 h. Basic workup as described above and distillation yielded 14.37 g (61%) of the title product, bp 62–63° C./20 mm Hg. $^1H$ NMR ($CDCl_3$) δ0.85 (t, J=6.2 Hz, 6H, $CH_3$), 1.01 (s, 9H, $CH_3$), 1.40 (sextet, J=6.2 Hz, 4H, $CH_2$), 2.3 6 (m, 4H, $CH_2$).

EXAMPLE 4 tert-Butyl-bis(2-methoxyethyl)amine (1d)

Dimethyl sulfate (50.45 g, 0.4 mol) was added dropwise to a vigorously stirred mixture of N-tertbutyldiethanolamine (16.13 g, 0.1 mol), dichloromethane (100 ml) tetrabutylammonium bromide (3.22 g, 10 mmol) and 50% aqueous sodium hydroxide (80 g, 1 mol at 30–40° C. The stirring was continued for 1 h after the addition was completed. The organic solution was separated and the aqueous layer was extracted with dichltromethane (25 ml). The organic solutions were combined. GC analysis showed a mixture of mono- and diethylated product. The methylation was repeated using the same amounts of reagents as described above. The dichloromethane solution after the second workup was stirred with concentrated aqueous ammonia (50 ml) for 1 h at room temperature, separated, dried over anhydrous magnesium sulfate and the product was isolated by distillation to yield 17.00 g, (90%), bp 42–44° C./0.1 mm/Hg; $^1$H NMR (CDCl$_3$) δ1.60 (s, 9H, CH$_3$), 2.70 (t, J=6.0 Hz, 4H, CH$_2$), 3.35 (s, 6H, CH$_3$), 3.37 (t, J=6.0 Hz, 4H, CH$_2$)

EXAMPLE 5 tert-Butylisobutylmethylamine (2a)

A 37% solution of formaldehyde (6.89 g, 85 mmol) was added dropwise to a mixture of tert-butylisobutylamine (10.00 g, 77 mmol) and 88% formic acid (7.85 g, 0.15 mol) at room temperature. The mixture was heated at 50–55° C. for 5 h. Aqueous 8 M potassium hydroxide (12.5 ml, 0.1 mol) was added, the organic layer was separated and the aqueous layer was extracted with n-pentane (50 ml). The extract was combined with the organic layer and dried over anhydrous magnesium sulfate. The product was isolated by distillation to yield 9.25 g, (84%), bp 44–45° C./18 mm Hg; $^1$H NMR (CDCl$_3$) δ0.85 (d, J=6.7 Hz, 6H, CH$_3$), 1.01 (s, 9H, CH$_3$), 1.64 (nonet, J=6.7 Hz, 1H, CH), 2.02 (d, J=6.7 Hz, 2H, CH$_2$), 2.15 (s, 3H, CH$_3$).

EXAMPLE 6 tert-Butylisobutylethylamine

A mixture of tert-butylisobutylamine (25.84 g, 0.2 mol) and diethyl sulfate (46.26 g, 0.3 mol) was warmed to 70° C. with stirring. An exothermic reaction started and in a few minutes the temperature rose to 150° C. with vigorous boiling of the mixture. After cooling to ~50° C., 5 M aqueous potassium hydroxide (100 ml, 0.5 mol) was added. The organic layer was separated and dried over anhydrous magnesium sulfate. Diethyl sulfate (10 ml) was added and the mixture was stirred at 100° C. for 1 h. Aqueous 5 M potassium hydroxide (100 ml) was added and the mixture was stirred at 80° C. for 1 h. The organic layer was separated and the aqueous layer was extracted with diethyl ether (50 ml). The organic solutions were combined, dried over anhydrous magnesium sulfate and the product was isolated by distillation. A small amount (1–2%) of tert-butylisobutylamine which was removed by the addition of 2.5 M n-butyllithium in hexane (5.0 ml, 10 mmol) and the product distilled to yield 22.56 g, (72%) of product, bp 68–70° C./40 mm Hg; $^1$H NMR (CDCl$_3$) δ0.85 (d, J=6.5 Hz, 6H, CH$_3$), 0.98 (t, J=6.5 Hz, 3H, CH$_3$), 1.01 (s, 9H, CH$_3$), 1.66 (n, J=6.5 Hz, 1H, CH), 2.04 (d, J=6.57 Hz, 2H, CH$_2$), 2.51 (q, J=6.5 Hz, 2H, CH$_2$).

EXAMPLE 7 tert-Butylisobutyl-n-propylamine (2d)

A mixture of tert-butylisobutylamine (19.39 g, 0.15 mol), 1-iodopropane (20.40 g, 0.12 mol) and glycerol (5.53 g, 60 mmol) was refluxed for 40 h. Aqueous 8 M potassium hydroxide (30 ml, 0.24 mol) was added, the organic layer was separated and the aqueous layer was extracted with n-pentane (50 ml). The organic solutions were combined, dried over anhydrous magnesium sulfate and the product was isolated by distillation to yield 12.52 g, (61%), bp 72–73° C./18 mm Hg; $^1$H NMR (CDCl$_3$) δ0.80 (t, J=6.2 Hz, 3H, CH$_3$), 0.84 (d, J=6.6 Hz, 6H, CH$_3$), 1.01 (s, 9H, CH$_3$), 1.40 (sextet, J=6.2 Hz, 2H, CH$_2$), 159 (nonet, J=6.6 Hz, 1H, CH), 2.16 (d, J=6.6 Hz, 2H, CH$_2$), 2.34 (m, 2H, CH$_2$).

EXAMPLE 8 tert-Butyldiisobutylamine (1e)

Isobutyryl chloride (10.90 g, 0.1 mol) was added to a solution of tert-butylisobutylamine (25.85 g, 0.2 mol) in tetrahydrofuran (150 ml) at room temperature and stirred for 1 h. Solids were filtered off and washed with tetrahydrofuran (2×25 ml). N, N-tert-butylisobutyl-2-methylpropionamide was isolated by distillation to yield 18.50 g, (90%), bp 59–60° C./1.3 mm Hg. A 1 M borane-tetrahydrofuran solution (100 ml, 0,10 mol) was added dropwise to a solution of the amide (17.95 g, 90 mmol) in tetrahydrofuran (50 ml) at room temperature and the mixture refluxed for 1 h. Water (5 ml) was added after cooling, followed by a slow addition of 6 M hydrochloric acid (60 ml). Tetrahydrofuran was distilled off and solid sodium hydroxide (20.00 g, 0.5 mol) was added. The organic layer was separated and the aqueous solution was extracted with n-pentane (50 ml). The organic solutions were combined, dried over anhydrous magnesium sulfate, and the product was isolated by distillation to yield 14.24 g, (85%), bp 34–35° C./1.5 mm Hg; $^1$H NMR (CDCl$_3$) δ0.84 (d, J=6.6 Hz, 12H, CH$_3$), 1.01 (s, 9H, CH$_3$), 1.58 (nonet, J=6.6 Hz, 2H, CH), 2.14 (d, J=6.6 Hz, 4H, CH$_2$),

EXAMPLE 9 tert-Butylisopropylethylamine (2e)

A mixture of tert-butylisopropylamine (11.5 g, 0.1 mol) and diethyl sulfate (15.42 g, 0.1 mol) was refluxed for 2 h. Aqueous 8 M potassium hydroxide (20 ml, 0.16 mol) was added and the organic layer was separated. The aqueous layer was extracted with n-pentane (20 ml). The organic solutions were combined, dried over magnesium sulfate, and the product was isolated by distillation: 7.16 g, (50%), bp 140–142° C.; $^1$H NMR (CDCl$_3$) δ0.99 (m, J=6.2 Hz, 9H, CH$_3$), 1.10 (s, 9H, CH$_3$), 2.55 (q, J=6.2 Hz, 2H, CH$_2$, 3.35 (septet, J=6.2, 1H, CH).

EXAMPLE 10 tert-Octyldiethylamine (3d)

Diethyl sulfate (18.50 g, 0.12 mol) was added to tert-octylamine (12.93 g, 0.1 mol) at room temperature. An exothermic reaction starts and the temperature increased to 120° C. After cooling to 50° C., aqueous 8 M potassium hydroxide (40 ml, 0.32 mol) was added, the organic layer was separated when warm and dried over anhydrous magnesium sulfate. The crude product was treated with diethyl sulfate (18.50 g, 0.12 mol) and heated with stirring at 100–150° C. for 15 min. After the same workup as described above, the organic layer was separated, dried over anhydrous magnesium sulfate and heated at 120° C. for 30 min. Basic workup as above and distillation gave the product: 16.66 g, (90%), bp 88–89° C./17 mm Hg; $^1$H NMR (CDCl$_3$) δ0.99 (s, 9H, CH$_3$), 1.02 (t, J=7.0 Hz, 6H, CH$_3$), 1.13 (s, 6H, CH$_3$), 1.40 (s, 2H, CH$_2$), 2.53 (q, J=7.0 Hz, 4H, CH$_2$).

EXAMPLE 11 tert-Octyldimethylamine (3a)

Formic acid, 88%, (20.92 g, 0.4 mol) was added to tert-octylamine (12.93 g, 0.1 mol) followed by a 37% formaldehyde solution (17.83 g, 0.22 mol) at 0° C. The mixture was warmed to 50–55° C. and kept at this temperature for 2 h. Aqueous 8 M potassium hydroxide (65 ml, 0.52 mol) was added and the mixture was extracted with n-pentane (2×50 ml). The pentane solution was dried over anhydrous magnesium sulfate and the product was isolated by distillation: 12.44 g (77%), bp 62–63° C./17 mm Hg; $^1$H NMR (CDCl$_3$) δ1.00 (s, 9H, CH$_3$), 1.11 (s, 6H, CH$_3$), 1.39 (s, 2H, CH$_2$), 2.21 (s, 6H, CH$_3$).

EXAMPLE 12

Quantitative Generation of Diborane

A 50-ml one-neck, round-bottom flask provided with a septum inlet, magnetic stirring bar and an adapter with a stopcock was charged with boron trifluoride-diglyme or -triglyme adduct (75 mmol). A 2 M solution of sodium borohydride in triglyme (28.5 ml, 57 mmol) was added dropwise by means of a hypodermic syringe. Generation of diborane is smooth and the reaction is not exothermic. After the addition was completed, the flask was heated to 100° C. and kept at this temperature for 15 min. Diborane was absorbed in tetrahydrofuran (30 ml) at 0° C. Analysis of the BH$_3$.THF solution obtained for active hydride according to a standard procedure described in Brown, H. C., *Organic Syntheses via Boranes;* J. Wiley: New York, 1975, p. 241, showed 2.37 M concentration of borane (95% yield) ; $^{11}$B NMR, δ, +1.0 ppm.

EXAMPLE 13

General Procedure for Preparation of Borane-Trialkylamine Adducts

Diborane (Example 12) was passed into a neat amine (50 mmol) at 0° C., contained in a flask fitted with a sintered glass inlet, a magnetic stirring bar and an exit bubbler. Excess diborane not absorbed by the amine passed through the mercury in the bubbler and dissolved in the next bubbler containing tetrahydrofuran (10 ml) overlaying the mercury, cooled in ice water. A second mercury bubbler was placed in series with the bubbler containing the tetrahydrofuran. Inlet tubes fitted with rubber serum caps were fitted to the flask containing the amine and to the bubbler containing the mercury overlaid with THF so that small samples of the borane-amine and the THF solution containing excess diborane can be removed by hypodermic syringes for analysis without opening the system to the atmosphere. The entire apparatus was flushed with nitrogen or argon and maintained under an inert atmosphere until the preparation of the borane-trialkylamine adduct had been completed and the product had been transferred to a suitable storage flask under an inert atmosphere.

Diborane was passed into the amine until the concentration of excess borane in the THF was ~1 M. A small sample of the amine-borane adduct was removed with a hypodermic syringe and analyzed. Then the flask containing the borane adduct was allowed to stand at room temperature and liberation of diborane, if any, noted on the bubbler. Small samples of the borane-amine and the THF solution above the bubbler were removed with syringes and analyzed for active hydrogen using a 2 M hydrochloric acid-glycerol-water (2:1:1) hydrolysis solution. This provided information to calculate the molarity of the borane-amine formed at 0° C. and at 25° C. A sample of the amine-borane was placed in an NMR tube and the $^{11}$B spectrum determined.

EXAMPLE 14

Borane-tert-butylisobutylethylamine Adduct

In the flask of the apparatus described in Example 13 was placed 50 mmol of tert-butylisobutylethylamine. The flask was cooled to 0° C. by immersion in an ice bath. The apparatus was flushed with nitrogen or argon and an inert atmosphere maintained. Diborane, generated as described in Example 12, was passed into the amine until no more was being dissolved. Removal of a small sample of the liquid product with a hypodermic syringe indicated the molarity of the borane in the amine was 4.4. The flask was allowed to warm to room temperature overnight. Only trace amounts of diborane passed through the bubbler. At room temperature, a second aliquot was removed and analyzed. The molarity of the borane was the same: 4.4. The borane and amine were in a ratio of 1:1. A sample of the amine-borane was placed in an NMR tube and the $^{11}$B NMR spectrum determined. Only one boron component was present, with δ=−14.71.

A sample of the borane-tert-butylisobutylethylamine (10 adduct (10 mmol) was added to the THF containing 30 mmol of 1-octene and the reaction followed by $^{11}$B NMR. In 20 minutes, the peak at δ=−14.71 had disappeared and the broad peak (singlet, 8.86 ppm) characteristic of n-octyl$_3$B had appeared.

EXAMPLE 15

Borane-tert-butylisopropylmethylamine

The apparatus described in Example 13 was assembled, flushed with nitrogen and a nitrogen atmosphere maintained throughout the process. In the flask was placed 50 mmol of tert-butylisopropylmethylamine and the flask cooled to 0° C. Diborane was passed in. The procedure described in Example 14 was followed. The liquid product exhibited a molarity of 5.3 The $^{11}$B NMR spectrum of the adduct in tetrahydrofuran revealed a single peak at δ−16.23. In tetrahydrofuran hydroboration of 1-octene by borane-t-butylisopropylmethylamine is fast and complete in 30 minutes forming n-trioctyl borane quantitatively.

EXAMPLE 16

Borane-tert-butylisopropylethylamine

In the flask of the apparatus described in Example 13 was placed 50 mmol of tert-butylisopropylethylamine. The flask was cooled to 0° C. by immersion in an ice-bath. The apparatus was flushed with nitrogen or argon and an inert atmosphere maintained throughout. Diborane, generated as described in Example 12, was passed into the amine until no more was being dissolved. Removal of a small sample of the liquid product with a hypodermic syringe indicated the molarity of the borane in the amine to be 5→3 M. The $^{11}$B NMR spectrum of the adduct in tetrahydrofuran revealed a single peak at δ−14.14 Hydroboration of 3 molar equivalents of 1-octene in tetrahydrofuran by the borane-tert-butylisopropylethylamine adduct was very fast, providing a quantitative yield of n-trioctyl borane in 15 minutes.

EXAMPLE 17

Borane-tert-butyl-bis(2-methoxyethyl)amine Adduct

In the flask of the apparatus described in Example 13 was placed 50 mmol of tert-butyl-bis(2-methoxyethyl)amine.

The flask was cooled to 0° C. by immersion in an ice bath. The apparatus was flushed with nitrogen or argon and an inert atmosphere maintained. Diborane, generated as described in Example 12, was passed into the amine until no more was being dissolved. Removal of a small sample of the liquid product with a hypodermic syringe indicated the molarity of the borane in the amine was 4.5. The flask was allowed to warm to room temperature overnight. Only trace amounts of diborane passed through the bubbler. At room temperature, a second aliquot was removed and analyzed. The molarity of the borane was the same: 4.5. The borane and amine were in a ratio of 1:1. A sample of the amine-borane was placed in an NMR tube and the $^{11}$B NMR spectrum determined. Only one boron component was present, with δ–14.26.

A 10-mmol sample of the adduct was added to the THF containing 30 mmol of 1-octene and the reaction followed by $^{11}$B NMR. In 30 minutes, the peak at δ–14.26 had disappeared and the broad peak characteristic of n-octyl$_3$B had appeared.

EXAMPLE 18

Borane-tert-octyldiethylamine Adduct

In the flask of the apparatus described in Example 13 was placed 50 mmol of tert-octyldiethylamine. The flask was cooled to 0° C. by immersion in an ice bath. The apparatus was flushed with nitrogen or argon and an inert atmosphere maintained. Diborane, generated as described in Example 12, was passed into the amine until no more was being dissolved. Removal of a small sample of the liquid product with a hypodermic syringe indicated the molarity of the borane in the amine was 4.0. The flask was allowed to warm to room temperature overnight. Only trace amounts of diborane passed through the bubbler. At room temperature, a second aliquot was removed and analyzed. The molarity of the borane was the same: 4.0. The borane and amine were in a ratio of 1:1. A sample of the amine-borane was placed in an NMR tube and the $^{11}$B NMR spectrum determined. Only one boron component was present, with δ=–15.14.

A 10-mmol sample of the adduct was added to the THF containing 30 mmol of 1-octene and the reaction followed by $^{11}$B NMR. In 20 minutes, the peak at δ–15.14 had disappeared and the broad peak characteristic of n-octyl$_3$B had appeared.

EXAMPLE 19 tert-Octyldi-n-propylamine

The title compound was prepared by the method of Example 18, substituting 50 mmol of tert-octyldi-n-propylamine for tert-octyldiethylamine. The product was a solid, mp 43–45° C. The borane and amine were in a ratio of 1:1. A sample of the amine-borane was placed in an NMR tube and the $^{11}$B NMR spectrum determined. Only one boron component was present, with δ–14.32.

A 10-mmol sample of the adduct was added to the THF containing 30 mmol of 1-octene and the reaction followed by $^{11}$B NMR. In 20 minutes, the peak at δ–14.32 had disappeared and the broad peak characteristic of n-octyl$_3$B had appeared.

EXAMPLE 20

Borane Adducts of Intermediate tert-alkyl Tertiary Amines

In this application the results are achieved with the borane adducts of tertiary amines derived from tert-butyldialkylamines and tert-octyldialkylamines. Similar results can be achieved by using intermediate tert-alkyl groups such as tert-pentyl, tert-hexyl, tert-heptyl, isopropyldimethyl, etc. Consequently, these derivatives are not described in detail herein.

EXAMPLE 21

Hydroboration of Representative Alkenes

The hydroboration characteristics of these new borane adducts are very similar to those previously observed for borane-tetrahydrofuran, borane-dimethyl sulfide and borane-1, 4-thioxane. Typical terminal olefins such as 1-pentene, 1-hexene, 1-octene, 2-methyl-1-butene, vinylcyclohexene, styrene and the like under hydroboration in the ratio of 3 alkene: 1 BH$_3$ to give R$_3$B.

Typical internal alkenes such as 2-butene, 3-hexene, cyclopentene, cyclohexene, cyclooctene, norbornene, and β-pinene undergo hydroboration in the ratio of 3 olefins: 1 BH$_3$ to give R$_3$B.

Trisubstituted olefins such as 2-methyl-2-butene, 1-methylcyclopentene, 1-methylbicyclohexene, and α-pinene undergo hydroboration to the R$_2$BH stage, i.e. in a ratio of 2 olefins: 1 BH$_3$.

More hindered olefins, such as 2,3-dimethyl-2-butene and 2,4,4-trimethyl-2-pentene, undergo hydroboration in a ration of 1 olefin: 1 BH$_3$, giving RBH$_2$.

EXAMPLE 22

General Procedure for Hydroboration of 1-Octene With Borane-Amine Adducts

1-Octene (3.36 g, 30 mmols) was added dropwise with stirring to a solution of a borane-amine adduct (10 mmols) in tetrahydrofuran (10.0 ml) at 25–28° C. The progress of the reaction was monitored by $^{11}$B NMR. The reaction was completed when the borane-amine signal (quartet) disappears and the trioctylborane signal (singlet, δ86 ppm) was the only one in the spectrum.

Tables 1–3 summarize the physical data for representative compounds disclosed and claimed herein. As can be seen from the following data, the preferred novel hydroboration agents of this invention meet the requirements of hydroborating 1-octene in tetrahydrofuran at room temperature in less than one hour; were liquid adducts of high borane concentration, stable at room temperature and soluble in representative solvents. Thus, they provide a valuable contribution to the art.

TABLE 1

Borane Adducts with t-BuNR$_2$

| | exchange,[a] % | | amine.BH$_3$ | | | | |
|---|---|---|---|---|---|---|---|
| | | | state[b] | [BH$_3$][c] | $^{11}$B NMR[d] | hydroboration of 1-octene[e] | |
| amine | BH$_3$.SMe$_2$ | BH$_3$.THF | (mp, °C.) | M | (δ) | in THF[f] | neat |
| t-BuN(CH$_2$CH$_2$)$_2$O<br>1a | 100 | 100 | | | −16.88 | 6 h | |
| t-BuNEt$_2$<br>1b | 85 | 100 | | | −14.89 | 6 h | |
| t-BuNPr$^n$$_2$<br>1c | 70 | 100 | | | −14.13 | 3 h | |
| t-BuN(CH$_2$CH$_2$OMe)$_2$<br>1d | 50 | 95 | liquid | 4.5 | −14.26 | 30 min | 1 h |
| t-BuNBu$^i$$_2$<br>1e | 0 | 0 | | | | | |

[a]Amine mixed with BH$_3$.SM$_2$ or 1M BH$_3$.THF in 1:1 molar ratio at room temperature and analyzed by $^{11}$B NMR at equilibrium.
[b]At 0° C.
[c]Estimated by hydrolysis in 2M HCl-glycerol-water (2:1:1) and measuring the hydrogen evolved.
[d]From the exchange with BH$_3$.SMe$_2$.
[e]5% excess of 1-octene, room temperature.
[f]3M solution of 1-octene and 1M in BH$_3$.

TABLE 2

Borane Adducts with t-BuNR$_2$

| | exchange,[a] % | | amine.BH$_3$ | | | | |
|---|---|---|---|---|---|---|---|
| | | | state[b] | [BH$_3$][c] | $^{11}$B NMR[d] | hydroboration of 1-octene[e] | |
| amine | BH$_3$.SMe$_2$ | BH$_3$.THF | (mp, °C.) | M | (δ) | in THF[f] | neat |
| t-BuNBu$^i$Me<br>2a | 73 | 100 | | | −14.13 | 20 h | |
| t-BuNPr$^i$Me<br>2b | 50 | 90 | liquid | 5.3 | −16.23 | 30 min | 3 h |
| t-BuNBu$^i$Et<br>2c | 33 | 73 | liquid | 4.4 | −14.71 | 20 min | 2 h |
| t-BuNBu$^i$Pr$^n$<br>2d | 24 | 71 | | | −14.10 | 20 min | |
| 1,2,2,6,6-penta-<br>methylpiperidine | 8 | 51 | (78–80) | | −16.04 | 20 min | |
| t-BuNPr$^i$Et<br>2e | 0 | 32 | liquid | 5→3 | −14.14[g] | 15 min | 1 h |

[a]Amine mixed with BH$_3$.SMe$_2$ or 1M BH$_3$.THF in 1:1 molar ratio at room temperature and analyzed by $^{11}$B NMR at equilibrium.
[b]At 0° C.
[c]Estimated by hydrolysis in 2M HCl-glycerol-water (2:1:1) and measuring the hydrogen evolved.
[d]From the excahnge with BH$_3$.SMe$_2$.
[e]5% excess of 1-octene, room temperature.
[f]3M solution of 1-octene and 1M in BH$_3$.
[g]From the exchange with BH$_3$.THF, since no exchange occurred with BMS.

TABLE 3

Borane Adducts with t-OctNR$_2$ and t-OctNRR'

| | exchange,[a] % | | amine.BH$_3$ | | | | |
|---|---|---|---|---|---|---|---|
| | | | state[b] | [BH$_3$][c] | $^{11}$B NMR[d] | hydroboration of 1-octene[e] | |
| amine | BH$_3$.SMe$_2$ | BH$_3$.THF | (mp, °C.) | M | (δ) | in THF[f] | neat |
| t-OctNMe$_2$<br>3a | 85 | 94 | | | −11.40 | no | |
| t-OctNEtMe<br>3b | 77 | 100 | | | −15.60 | 24 h | |
| t-OctN(CH$_2$CH$_2$)$_2$O<br>3c | 50 | 87 | 96–97 | | −16.42 | 20 min | |

TABLE 3-continued

Borane Adducts with t-OctNR$_2$ and t-OctNRR'

| amine | exchange,[a] % | | state[b] | amine·BH$_3$ | | | hydroboration of 1-octene[e] | |
| | BH$_3$·SMe$_2$ | BH$_3$·THF | (mp, °C.) | [BH$_3$][c] M | $^{11}$B NMR[d] (δ) | | in THF[f] | neat |
|---|---|---|---|---|---|---|---|---|
| t-OctNEt$_2$ 3d | 38 | 88 | liquid | 4.0 | −15.14 | | 20 min | 3 h |
| t-OctNBu$^i$Me 3e | 35 | 88 | 48–50 | | −14.29 | | 1.5 h | |
| t-OctNPr$^n{}_2$ 3f | 25 | 81 | 43–45 | | −14.32 | | 20 min | |

[a]Amine mixed with BH$_3$·SMe$_2$ or 1M BH$_3$·THF in 1:1 molar radio at room temperature and analyzed by $^{11}$B NMR at equilibrium.
[b]At 0° C.
[c]Estimated by hydrolysis in 2M HCl-glycerol-water (2:1:1) and measuring the hydrogen evolved.
[d]From the exchange with BH$_3$·SMe$_2$.
[e]5% excess of 1-octene, room temperature.
[f]3M solution of 1-octene and 1M in BH$_3$.

What is claimed is:

1. tert-Octyldi-n-proplylamine.

2. tert-Octyl-N-morpholine-borane.

* * * * *